(12) United States Patent
Ishii et al.

(10) Patent No.: US 11,974,850 B2
(45) Date of Patent: *May 7, 2024

(54) NAME TAG TRANSMITTER, SMARTWARE MANAGEMENT SYSTEM, AND SMARTWARE MANAGEMENT METHOD

(71) Applicant: Nippon Telegraph and Telephone Corporation, Tokyo (JP)

(72) Inventors: Yuzo Ishii, Tokyo (JP); Toshishige Shimamura, Tokyo (JP); Rena Nakatsuji, Tokyo (JP); Hitoshi Okikawa, Tokyo (JP); Yoshiyuki Doi, Tokyo (JP); Nobutomo Yoshihashi, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 148 days.

This patent is subject to a terminal disclaimer.

(21) Appl. No.: 17/625,144

(22) PCT Filed: Jul. 10, 2019

(86) PCT No.: PCT/JP2019/027303
§ 371 (c)(1),
(2) Date: Jan. 6, 2022

(87) PCT Pub. No.: WO2021/005740
PCT Pub. Date: Jan. 14, 2021

(65) Prior Publication Data
US 2022/0265191 A1 Aug. 25, 2022

(51) Int. Cl.
*A61B 5/256* (2021.01)
*A61B 5/00* (2006.01)
*G06K 19/077* (2006.01)
*G16H 10/65* (2018.01)
*G16H 40/20* (2018.01)
*G16H 40/63* (2018.01)
*H04W 4/80* (2018.01)

(52) U.S. Cl.
CPC ............ *A61B 5/256* (2021.01); *A61B 5/0015* (2013.01); *G06K 19/07705* (2013.01);
(Continued)

(58) Field of Classification Search
CPC ....... A61B 5/256; A61B 5/486; A61B 5/0022; G16H 10/65; G07C 2009/00809
See application file for complete search history.

(56) References Cited

U.S. PATENT DOCUMENTS

2009/0171233 A1 7/2009 Lanfermann et al.
2016/0155281 A1* 6/2016 O'Toole ................ H04W 12/50
340/5.64
(Continued)

FOREIGN PATENT DOCUMENTS

JP 2011056243 A 3/2011
JP 2017207851 A 11/2017
KR 20190041239 A 4/2019

OTHER PUBLICATIONS

Homer Ion Lab Co., Ltd., Literature "Introducing G-TES equipped with B-SES Beacess for muscle electrical stimulation", Reading day: Jun. 11, 2019, ttp://www.homerion.co.jp/products/g-tes.html, 15 pages (with translation).

(Continued)

*Primary Examiner* — Mirza F Alam
(74) *Attorney, Agent, or Firm* — Slater Matsil, LLP

(57) ABSTRACT

A nametag transmitter is a nametag transmitter that is to be attached to smartwear including an electrode for detecting biological information, the nametag transmitter including: a reception unit for receiving the biological information from the electrode; a wireless communication unit for transmitting the biological information to a data collection apparatus; a display unit for displaying identification information for specifying a user of the smartwear; and a connection portion to be attached to the smartwear. The nametag
(Continued)

transmitter is attached to the smartwear in a state in which pairing between the wireless communication unit and the data collection apparatus has been carried out.

10 Claims, 8 Drawing Sheets

(52) U.S. Cl.
CPC ............ G16H 10/65 (2018.01); G16H 40/20 (2018.01); G16H 40/63 (2018.01); H04W 4/80 (2018.02)

(56) References Cited

U.S. PATENT DOCUMENTS

| | | | | |
|---|---|---|---|---|
| 2016/0308969 | A1* | 10/2016 | Aihara | G06F 16/951 |
| 2018/0234804 | A1* | 8/2018 | Takata | H04L 67/306 |
| 2018/0299991 | A1* | 10/2018 | Juhasz | B60R 13/02 |
| 2023/0165524 | A1* | 6/2023 | Larson | G16H 50/30 |
| | | | | 600/301 |

OTHER PUBLICATIONS

Nihon Medix Co., Ltd., Literature "Bio Monitor ME6000 (8CH)", Reading day: Jun. 11, 2019, https://www.nihonmedix.co.jp/products/details/prd_000042.php, 5 pages (with translation).

Nihon Medix Co., Ltd., Literature "Applications of muscle strength / functionevaluation measuring instrument", Reading day: Jun. 11, 2019, https://www.nihonmedix.co.jp/support/04assessment_index.html, 9 pages (with translation).

Og Wellness Tech Co., Ltd., Literature: "Electrical Stimulation Therapy IVES Ibis Plus GD-611 / Ibis GD-612", Reading day: Jun. 11, 2019, https://www.og-wellness.jp/product/medical/gd611-612, 11 pages (with translation).

* cited by examiner

| STORAGE BOX POSITION NUMBER | TRANSMITTER ID | SMARTPHONE ID | NAME | SITE |
|---|---|---|---|---|
| No.1 | 00-0B-5D-9C-74-24 | A | ○○ ○○ | CHEST INDUCTION (I INDUCTION) |
| NO.2 | 12-34-56-78-90-AB | B | ○○ ×○ | CHEST INDUCTION (I INDUCTION) |
| NO.3 | 003 | C | ○○ ×× | CHEST INDUCTION (I INDUCTION) |
| NO.4 | 001 | D | ○× ○○ | CHEST INDUCTION (I INDUCTION) |
| . . . . | . . . . | . . . . | . . . . | . . . . |

NAME TAG TRANSMITTER, SMARTWARE MANAGEMENT SYSTEM, AND SMARTWARE MANAGEMENT METHOD

CROSS-REFERENCE TO RELATED APPLICATIONS

This application is a national phase entry of PCT Application No. PCT/JP2019/027303, filed on Jul. 10, 2019, which application is hereby incorporated herein by reference.

TECHNICAL FIELD

The present invention relates to a system for managing smartwear for acquiring biological information of a patient, a worker, or the like at a medical facility, a work site, or the like.

BACKGROUND

Research and development has been progressing on a technique according to which biological information acquired by a wearable device (smartwear) worn by a patient or a worker is transmitted to an external system by a transmitter and a manager performs health management of the patient or the worker.

FIG. 9A shows an exemplary configuration of a conventional health management system. FIG. 9B shows an example of a work flow of a conventional health management system. In the conventional health management system, first, a user (patient) 1 puts on smartwear 2 in which an electrode for detecting a biological signal such as a vital signal is installed. Next, the user (patient) attaches a transmitter, which was given by medical staff (a therapist, a caregiver, an assistant, etc.) and is for transmitting data on biological information, to the smartwear. At this time, the transmitter has not been started up.

After the transmitter is attached, the medical staff carries out a system connection task for the transmitter such that it is possible to transmit data from the transmitter to a system such as a smartphone that performs data collection. First, the medical staff starts up the transmitter, turns on a wireless communication function (Bluetooth (registered trademark), etc.), and performs a pairing task between the smartphone and the transmitter. After the pairing task, a calculation start task is performed, and it is checked whether or not the biological information of the user is being transmitted normally, using a viewer function of the smartphone. After the above task is carried out, the user (patient) starts rehabilitation or the like.

CITATION LIST

Patent Literature

PLT 1—Japanese Patent Application Publication No. 2017-207851.

SUMMARY

Technical Problem

However, in the above-described operation flow, in the pairing task between the smartphone and the transmitter, if there is a transmitter nearby whose wireless communication function has similarly been turned on, there is a possibility that the smartphone and that transmitter will be paired erroneously. It is thought that such a situation will occur if users are gathered in a specific room such as a rehabilitation room, if users gather near a nurse station to receive transmitters, or the like.

Also, if the medical staff performing the system connection task is not used to operating IT devices, if the pairing task needs to be performed rapidly since users (patients) have created a line waiting for the system connection task, or the like, the risk of a pairing error occurring increases. There is also a possibility that a pairing error will result in misidentifying a user (patient), and therefore will lead to a serious incident.

Furthermore, a situation can also occur in which, due to a measurement start operation of the transmitter being forgotten, biological information such as vital data cannot be acquired normally even though the smartwear is being worn. Note that although the startup of the transmitter and the pairing task can also be performed by the users themselves, the above-described risks will still be present.

Here, a case is also conceivable in which a data collection device that can simultaneously contain multiple sensors is used, as in PLT 1. Examples of the data collection device that is to be the target of pairing can include an IoT gateway device, as well as a smartphone that has multiple simultaneous pairing functions. In PLT 1, there is a problem in that the likelihood of causing a pairing error becomes higher since pairing is performed with multiple sensors.

described above, the conventional health management system is problematic in that the pairing task requires labor and there is a high risk of misidentifying a patient or user.

Embodiments of the present invention were made in view of this kind of problem and aims to provide a smartwear management system according to which it is possible to increase the efficiency of a pairing task and reduce the risk of misidentifying a user.

Means for Solving the Problem

In order to solve the above-described problems, a nametag transmitter of embodiments of the present invention is a nametag transmitter to be attached to smartwear including an electrode for detecting biological information, the nametag transmitter including: a reception unit configured to receive the biological information from the electrode; a wireless communication unit configured to transmit the biological information to a data collection apparatus; a display unit configured to display identification information for specifying a user of the smartwear; and a connection portion to be attached to the smartwear, in which the nametag transmitter is attached to the smartwear in a state in which pairing between the wireless communication unit and the data collection apparatus has been carried out.

In order to solve the above-described problems, a smartwear management system of embodiments of the present invention is a smartwear management system for managing smartwear including an electrode for detecting biological information, the smartwear management system including: a nametag transmitter including a reception unit configured to receive the biological information from the electrode, a wireless communication unit configured to transmit the biological information to a data collection apparatus, a display unit configured to display identification information for specifying a user of the smartwear, and a connection portion to be attached to the smartwear; a storage box in which the nametag transmitter is to be stored before being attached to the smartwear; and a management apparatus configured to associate and manage storage position information in the storage box, identification information of the nametag transmitter, identification information of the data collection apparatus paired with the wireless communication unit, and the identification information of the user.

In order to solve the above-described problems, a smartwear management method of embodiments of the present invention is a smartwear management method to be performed by a smartwear management system for managing smartwear including an electrode for detecting biological information, in which the smartwear management system includes: a nametag transmitter including a reception unit configured to receive the biological information from the electrode, a wireless communication unit configured to transmit the biological information to a data collection apparatus, a display unit configured to display identification information for specifying a user of the smartwear, and a connection portion to be attached to the smartwear; and a storage box in which the nametag transmitter is to be stored before being attached to the smartwear, and the smartwear management system associates and manages storage position information in the storage box, identification information of the nametag transmitter, identification information of the data collection apparatus paired with the wireless communication unit, and the identification information of the user.

Effects of Embodiments of the Invention

According to embodiments of the present invention, it is possible to provide a smartwear management system according to which it is possible to increase the efficiency of a pairing task and reduce the risk of misidentifying a user.

DETAILED DESCRIPTION OF ILLUSTRATIVE EMBODIMENTS

Hereinafter, embodiments of the present invention will be described with reference to the drawings. The present invention can be carried out in many different forms, and there is no limitation to embodiments of the present invention that will be described hereinafter.

Configuration and Operation Flow of Smartwear Management System

Figure 1A:
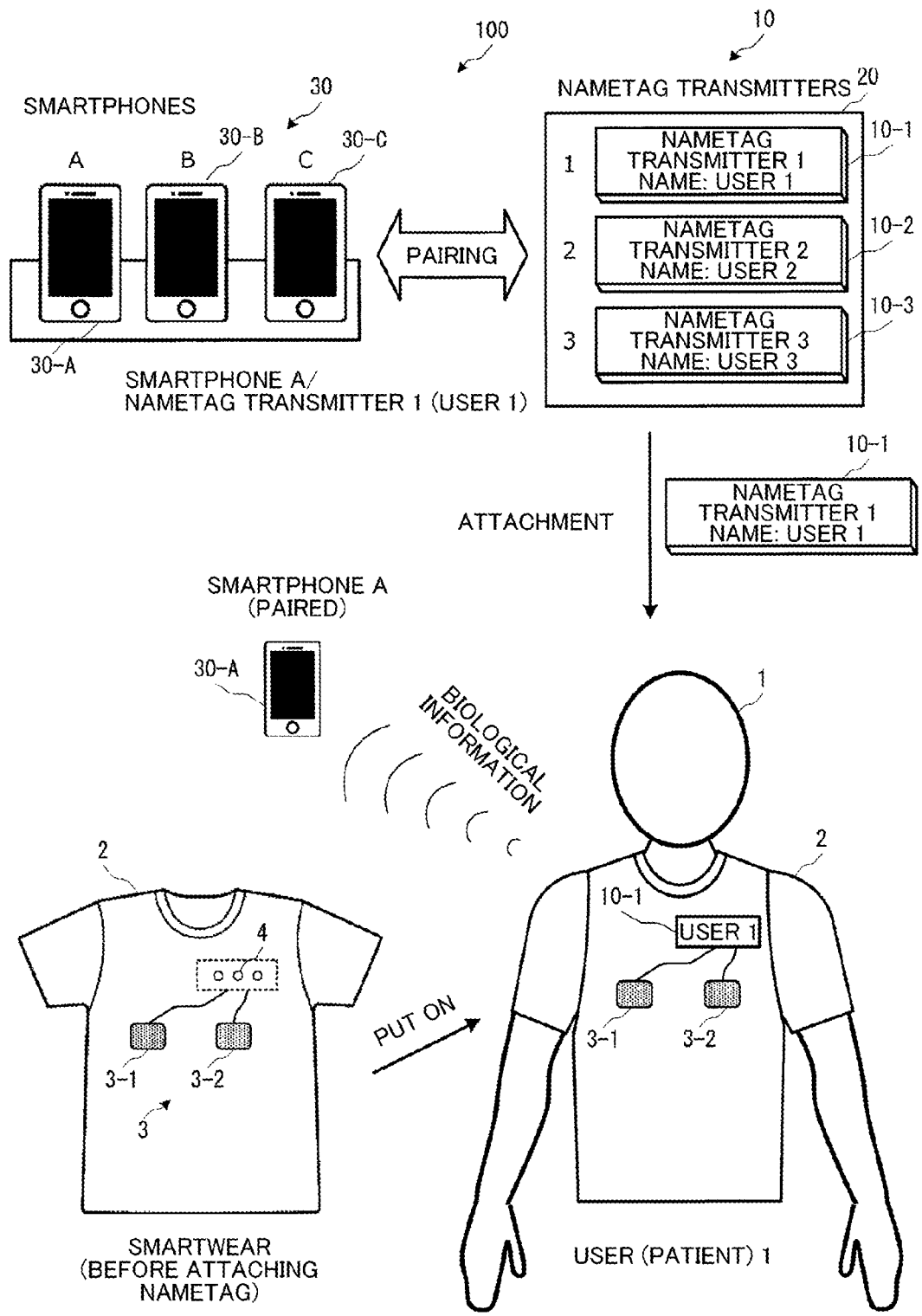
FIG. 1A is a diagram showing an exemplary configuration of a smartwear management system of embodiments of the present invention.

FIG. 1A is a diagram showing an exemplary configuration of a smartwear management system of embodiments of the present invention. Smartwear 2 includes electrodes 3 for detecting biological information and has a connection portion 4 for connecting a nametag transmitter 10. By attaching the nametag transmitter 10 to the smartwear 2, the biological information transmitted from the electrodes 3 can be transmitted to a data collection apparatus such as a smartphone 30.

A transmitter that transmits data on the biological information in embodiments of the present invention can display identification information of a user (patient), such as the name or personal ID of the user. The display of the identification information of the user may also be displayed electronically, or may be display performed by handwriting or attachment of a sticker. If the name of the user or the like has been written, the transmitter has the same appearance as a nametag, and therefore in the description of embodiments of the present invention, a transmitter displaying the identification information such as the name of the user (patient) will be referred to as a "nametag transmitter".

Nametag transmitters (10-1 to 10-3) are stored and managed in a centralized manner at a nurse center, an IT device management room, or the like, and are stored in a storage box 20. By storing and managing the nametag transmitters in a centralized manner, a list of future users, and the preparation status and stock information of the nametag transmitters 10 to be used thereby are clear at a glance, and therefore it is easy for the medical staff to manage the nametag transmitters 10. In embodiments of the present invention, the nametag transmitter (10-1) that has been paired with a smartphone (30-A) that is the transmission destination of the data of the biological information is attached to the smartwear 2.

Figure 1B:
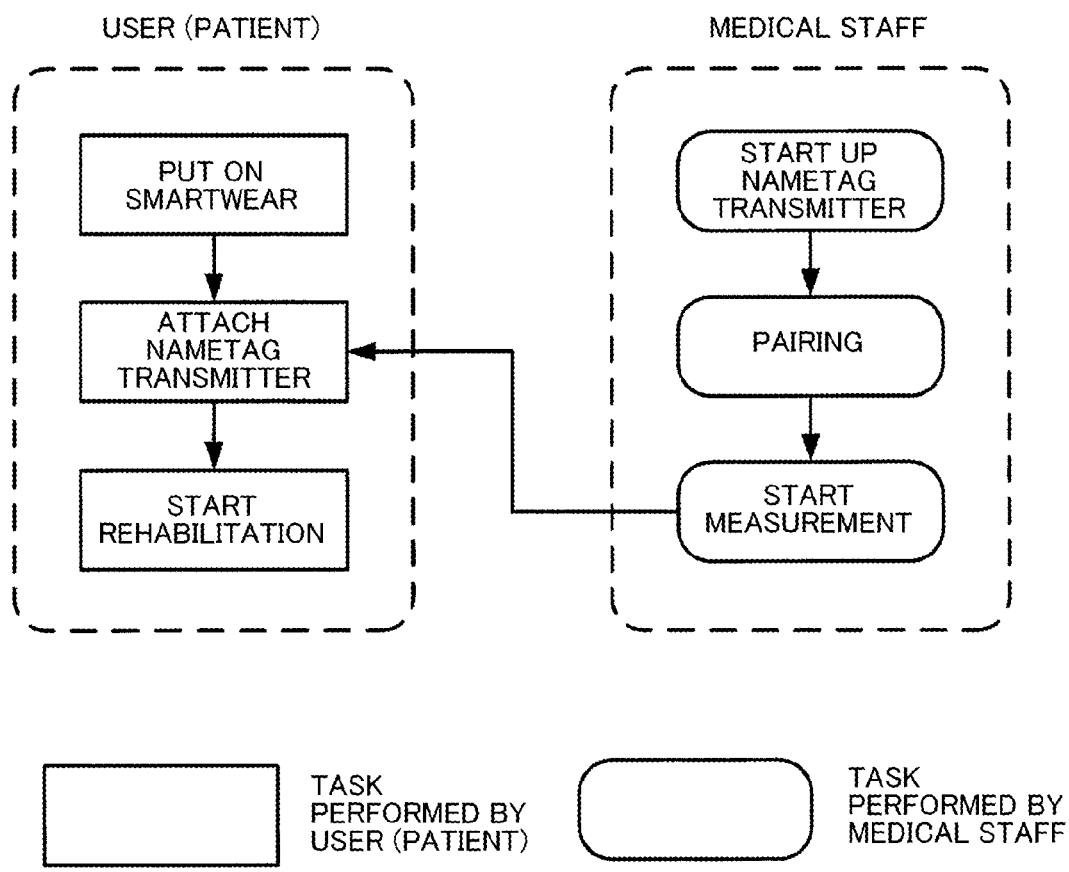
FIG. 1B is a diagram showing an exemplary work flow in the smartware management system of embodiments of the present invention.

FIG. 1B is a diagram showing an exemplary work flow of a smartwear management system of embodiments of the present invention. Before the users gather to perform rehabilitation training or the like, the medical staff starts up the nametag transmitters 10 and carries out the system connection task such as pairing in advance. At this time, the users of the nametag transmitters 10 have not yet shown up at the location of the rehabilitation training or the like, but since the names, which are the identification information of the users, have been written on the nametag transmitters 10, the pairing task can be performed with the nametag transmitters 10 representing the users before the nametag transmitters are attached.

Since the medical staff does not need to perform the pairing task for each person in front of the users, the medical staff can perform the task in a relaxed manner, and therefore the risk of performing a pairing error significantly decreases. Furthermore, the medical staff performs operations up to the measurement start operation before attaching the nametag transmitters 10 to the users. At this point in time, the nametag transmitters 10 are not attached to the smartwear of the users, and therefore the biological information such as the vital signals has not yet been acquired.

In the stage at which the pairing with the smartphones and the measurement start operation have been performed, the users are gathered in order to put on the nametag transmitters, and the nametag transmitters are given to the users. Smartwear that fits the size of each body is given in advance to the users and the users gather wearing the smartwear. If the users are hospitalized patients, the users may change clothes in their beds. If the users are outpatients, the users may receive the smartwear during reception and change clothes in a changing room, or by giving the smartwear to the users in advance, the users may come to the location of the rehabilitation training or the like after putting on the smartwear at their homes.

The medical staff gives the nametag transmitters to the users, the users check that their names are written on their nametag transmitters, and the users attach the nametag transmitters to their smartwear. Here, the nametag transmitters have already been paired and are in a measurement start state, and therefore acquisition of the biological information such as the vital signals is started at the time when the nametag transmitters are attached to the smartwear, and the data of the acquired biological information is transferred to the smartphones or the system.

Figure 9A:
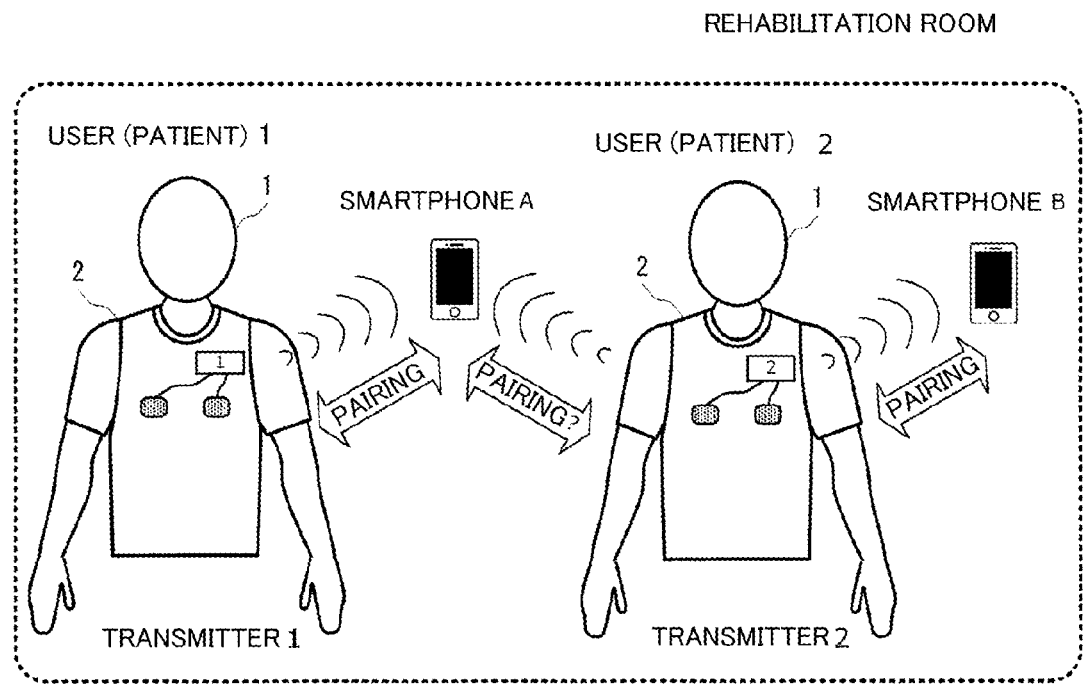
FIG. 9A is an exemplary configuration of a conventional health management system.
Figure 9B:
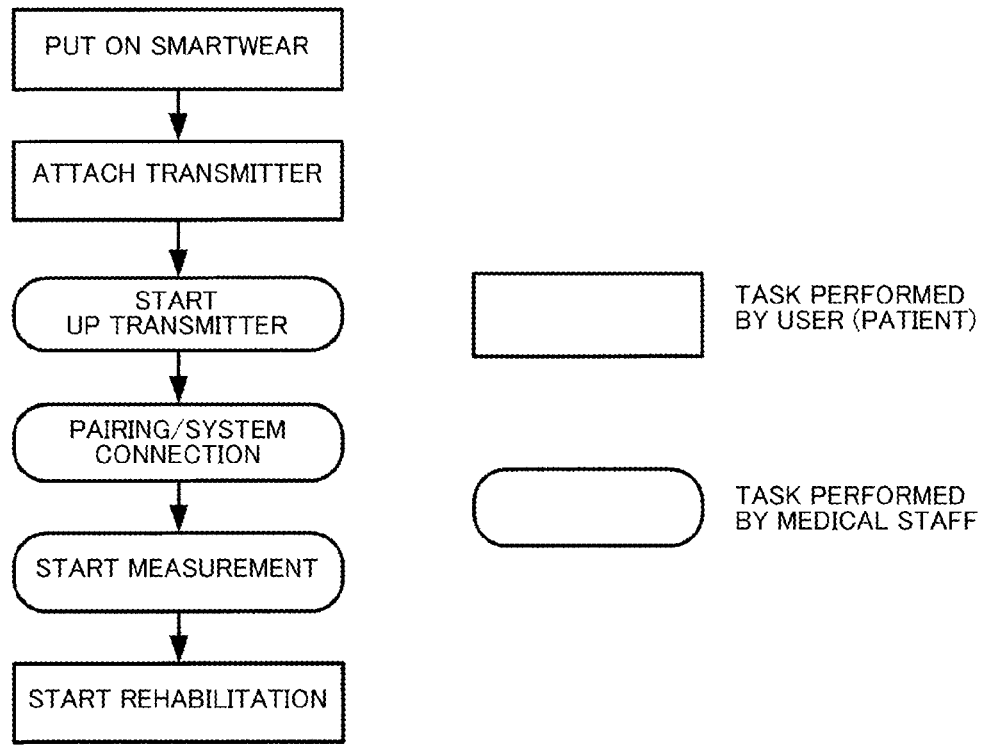
FIG. 9B is a diagram showing an exemplary work flow of the conventional health management system.

In the conventional work flow shown in FIG. 9B, tasks performed by a user and tasks performed by medical staff are both present, and therefore there has been a problem in that waiting time for the tasks occurs. On the other hand, in the work flow using the nametag transmitter of embodiments of the present invention, the tasks performed by the user and the tasks performed by the medical staff can be performed independently, and therefore it is possible to avoid a situation in which the user is made to wait for a long time, and the pairing task can be performed efficiently. Furthermore, with the nametag transmitter of embodiments of the present invention, the association with the user and the pairing with the smartphone have been carried out when the nametag transmitter is attached to the smartwear, and therefore the risk of misidentifying the user is also significantly reduced. Furthermore, by attaching the nametag transmitter in a state in which the measurement start operation has been performed, an effect of reducing the risk of measurement start omission as well is obtained.

Note that in the above-described work flow, a case was envisioned in which rehabilitation training is performed at a medical institution for rehabilitation patients, but the use target of embodiments of the present invention is not limited to rehabilitation training at a medical institution. Embodiments of the present invention can be applied also to the case of acquiring biological information using smartwear at a health examination, a complete medical checkup, a training gym, a work site, or the like. In this case, the above-described medical staff need only be replaced with facility staff, a work manager, or the like. In particular, if there is a large risk of misidentification, such as a case in which setting is performed for a large number of people (users) at once, it can be expected that the effect of embodiments of the present invention will be exhibited.

Configuration of Nametag Transmitter

Figure 2A:
FIG. 2A is a diagram showing an exemplary configuration (front surface) of a nametag transmitter of embodiments of the present invention.
Figure 2B:
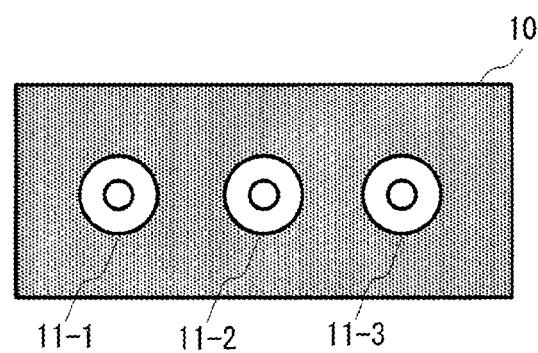
FIG. 2B is a diagram showing an exemplary configuration (rear surface) of the nametag transmitter of embodiments of the present invention.
Figure 2C:
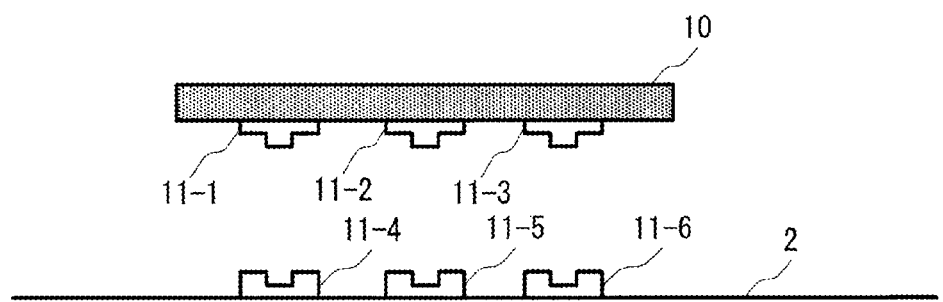
FIG. 2C is a diagram showing an exemplary configuration (cross section) of the nametag transmitter of embodiments of the present invention.

FIGS. 2A to 2C are diagrams showing an exemplary configuration of the nametag transmitter of embodiments of the present invention. A display unit 15 that can display identification information such as a name or a personal ID by which a user (patient) can be specified is included on the front surface of the nametag transmitter 10. The display unit 15 for the identification information of the user may also be a display that performs display electronically, or may be display performed through handwriting or attachment of a sticker. As shown in FIG. 2A, a display type according to which the on or off state of the power source, the battery remaining amount, and the like can be understood may also be equipped on the front surface of the nametag transmitter 10.

As shown in FIGS. 2B and 2C, connection portions (11-1 to 11-3) such as buttons or fasteners for attaching to the smartwear 2 are provided on the rear surface of the nametag transmitter 10. On the other hand, connection portions (11-4 to 11-6) are installed on the smartwear 2 in correspondence with the connection portions (11-1 to 11-3) on the nametag transmitter 10. The nametag transmitter 10 is attached to the smartwear 2 due to the connection portions (11-1 to 11-3) and the connection portions (11-4 to 11-6) connecting to each other. These connection portions (11-1 to 11-6) also carry out the role of electrical contacts for transmitting electrical signals detected in the electrodes 3 of the smartwear 2 to the nametag transmitter 10.

Figure 3:
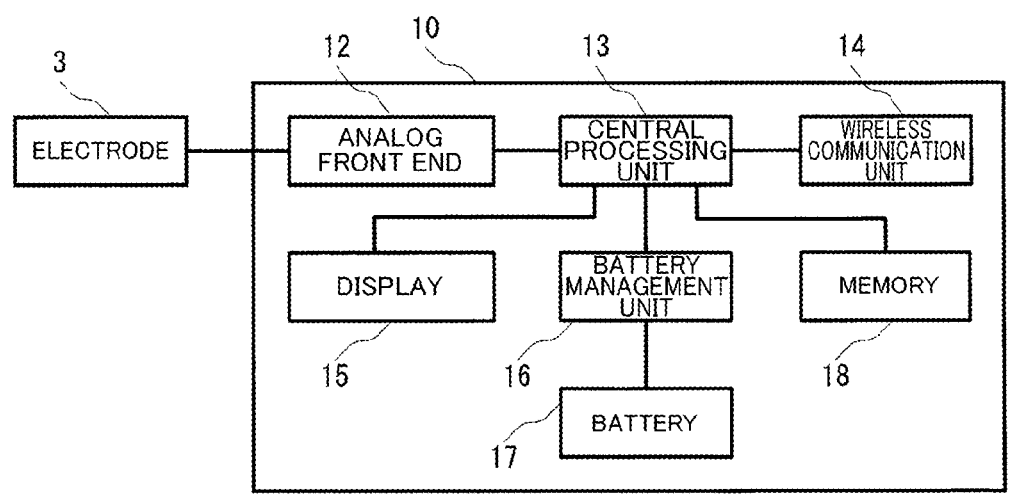
FIG. 3 is a diagram showing an exemplary configuration of the nametag transmitter of embodiments of the present invention.

As shown in FIG. 3, the nametag transmitter 10 is a reception unit that receives an electrical signal from an electrode, and is equipped with an analog front end circuit 12 that performs signal processing such as signal amplification, A/D conversion, and various types of filter processing, a wireless communication unit 14 that transmits the signal-processed biological information to a data collection apparatus such as a smartphone, a display 15, which is a display unit that can display identification information such as the name or personal ID of the user, a central processing unit 13 that performs control of the units, a battery management unit 16 and battery 17 for supplying power to the units, a memory 18 that stores the biological information and the like, and the like. The wireless communication unit 14 includes an antenna portion for transmitting a wireless signal. The wireless communication unit 14 performs communication with a data collection apparatus such as a paired smartphone, and performs communication with the later-described storage box 20 of the nametag transmitter.

Here, the processing of the central processing unit 13 may also be realized with software by a program stored in a memory or the like, and the functions of the central processing unit 13, the wireless communication unit 14, and the like may also be realized with hardware by an FPGA (field-programmable gate array).

First Embodiment

Figure 4:
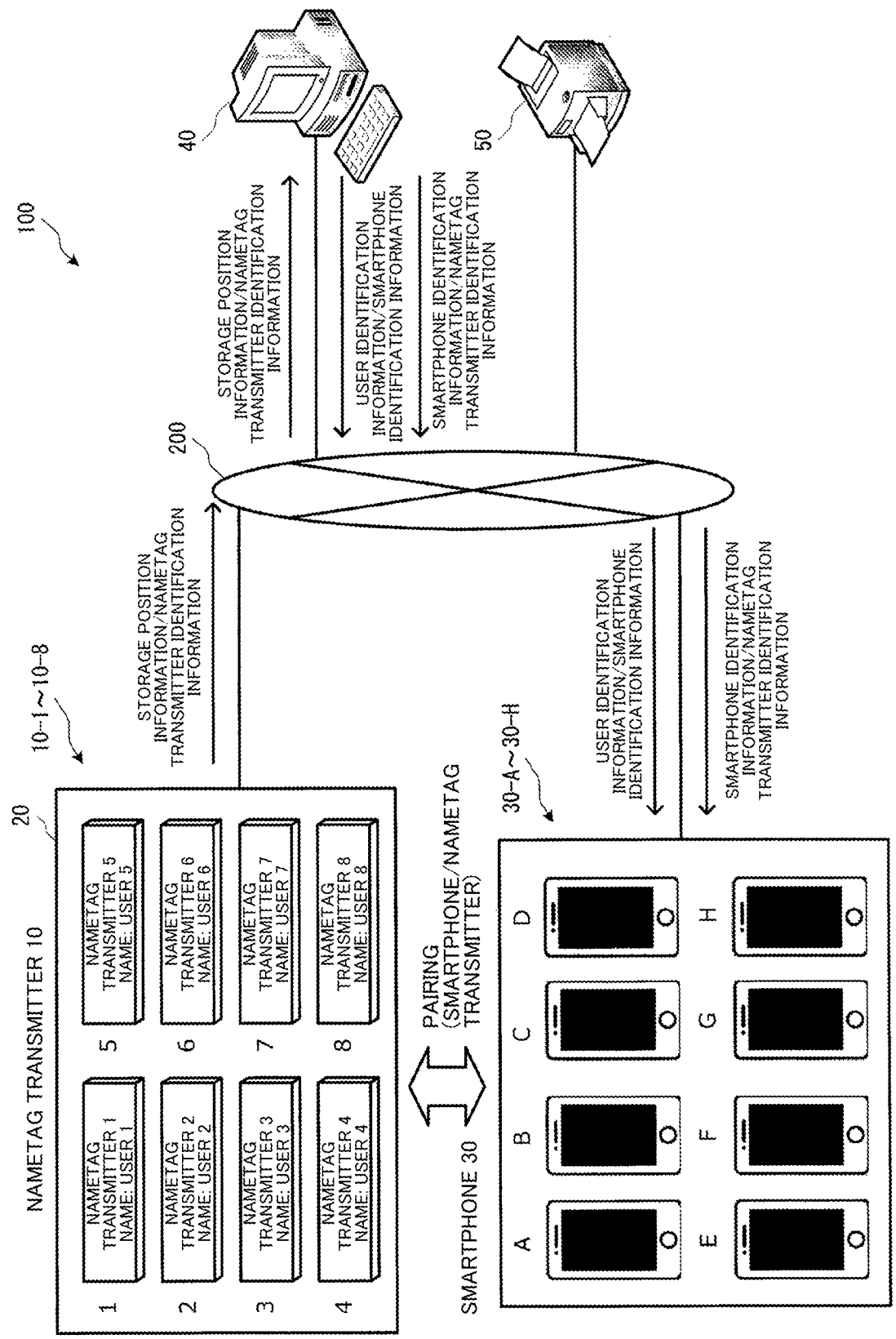
FIG. 4 is a diagram showing an exemplary configuration of a smartwear management system according to a first embodiment of the present invention.

FIG. 4 is a diagram showing an exemplary configuration of a smartwear management system according to a first embodiment of the present invention. A smartwear management system 100 is constituted by nametag transmitters (10-1 to 10-8), a storage box 20 in which the nametag transmitters (10-1 to 10-8) are stored before being attached to the smartwear 2, a management apparatus 40, and a printer 50. The management apparatus 40 associates and manages storage position information in the storage box 20, identification information of the nametag transmitter, identification information of a paired smartphone, and identification information of a user. The printer 50 is network-connected to a management apparatus or the like.

The nametag transmitters (10-1 to 10-8) are stored and managed in a storage box 20 such as that shown in FIG. 4 before being attached to the smartwear 2. The storage box 20 is equipped with a power supply function, and can charge the nametag transmitters (10-1 to 10-8) via a wireless power supply technique such as Qi, or electrical contacts. Dedicated power source connectors may also be used as the electrical contacts, and power may be supplied via the connection portions (11-1 to 11-3) on the rear surfaces of the nametag transmitters or the like. Also, the smartphones (30-A to 30-H) that are to be paired may also be stored in a stand or the like equipped with a power supply function.

The identification information of the nametag transmitters (10-1 to 10-8) is identification information that is unique to the nametag transmitters, such as MAC addresses, device names, or the like. The correspondence relationship between the storage position numbers of the storage box 20 and the identification information of the nametag transmitters (10-1 to 10-8) stored at the storage positions is configured to be checked automatically by connecting the storage box 20 and the nametag transmitters with a USB cable and performing communication therebetween. The correspondence relationship between the storage position numbers of the storage box 20 and the identification information of the stored nametag transmitters (10-1 to 10-8) can be transmitted to the management apparatus 40 through a network 200.

Figures 5, 6:
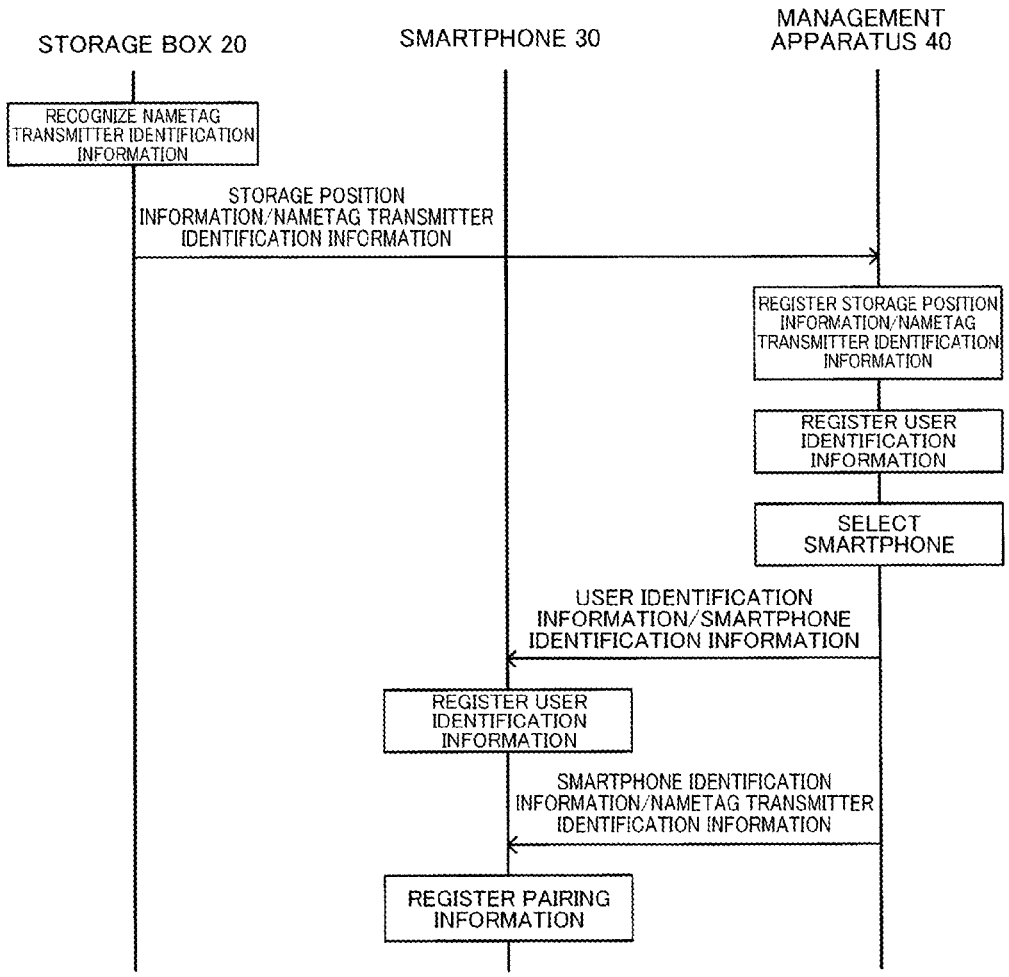
FIG. 5 is a diagram showing an exemplary configuration of a management screen according to the first embodiment of the present invention.
FIG. 6 is a diagram showing an exemplary operation sequence of a smartwear management method according to the first embodiment of the present invention.

The management apparatus 40 acquires the correspondence information between the storage position numbers of the storage box 20 and the identification information of the nametag transmitters from the storage box 20 through the network 200, and displays the correspondence information on a management screen. An example of the management screen is shown in FIG. 5. The medical staff checks the state of the nametag transmitters (10-1 to 10-8) stored in the storage box 20 on the management screen of the management apparatus 40. On the management screen, identification information (IDs) of the nametag transmitters (10-1 to 10-8) stored at the storage positions is displayed in rows corresponding to the storage position numbers (No. 1, No. 2, . . . ) in the storage box.

FIG. 6 is a diagram showing an exemplary operation sequence of a smartwear management method according to a first embodiment of the present invention. Identification information such as the names of patients (users) who are to perform rehabilitation or the like is registered in the management apparatus 40. This registration is not limited to manual input performed by the medical staff, and may also be performed such that the names of the users are selected from a database by linking with a database in a hospital, such as an electronic medical record system. In this case, it is possible to reference the medical record, rehabilitation history, and the like of the user in addition to the name of the user. The smartphones (30-A to 30-H) to be given to the users are selected after the names of the users are input. The smartphones (30-A to 30-H) need only be selected from a pull-down menu on the management screen of the management apparatus 40.

Here, in the setting of the correspondence information between the smartphone and the user in the smartphone, for example, the user may be selected in a smartphone application while checking the management screen, or the correspondence information between the identification information of the user and the smartphone may be transmitted from the management apparatus 40 to the smartphone (30-A to 30-H), so as to achieve an association set on the management screen.

The transmission of the correspondence information from the management apparatus 40 to the smartphone (30-A to 30-H) can be performed by connecting the stand in which the smartphones (30-A to 30-H) are stored and the smartphones (30-A to 30-H) with a USB cable or the like. The transmission may also be performed by connecting the management apparatus 40 and the smartphones (30-A to 30-H) using wireless communication such as a wireless LAN. As long as the identification information such as the names of the users is displayed on the smartphone screens, the medical staff can easily check that the correct association has been performed.

As shown in FIG. 5, the nametag transmitters (10-1 to 10-8) paired with the smartphones (30-A to 30-H) to be used by the users are associated and managed with the management apparatus 40. Based on this association, the pairing task between the smartphones (30-A to 30-H) and the nametag transmitters (10-1 to 10-8) is executed.

Although this pairing task may also be performed by medical staff operating a screen of a smartphone to select the identification information of the corresponding nametag transmitters (10-1 to 10-8) displayed on the management screen, the pairing information between the smartphones and the nametag transmitters may also be transmitted through wired communication or wireless communication from the management apparatus 40 to the smartphones (30-A to 30-H), similarly to the correspondence information between the users and the smartphones, so as to achieve the correspondence relationship displayed on the management screen.

Due to the pairing information between the smartphones (30-A to 30-H) and the nametag transmitters (10-1 to 10-8) being displayed on the screen of the smartphone, the medical staff can easily check that the correct pairing has been performed. It is also easy to collectively perform the pairings for multiple smartphones.

As stated above, the association between the users, the nametag transmitters, and the smartphones in the smartwear management system of the present embodiment is completed. According to the present embodiment, the smartphones to be used by the users and the nametag transmitters to be paired can be associated and managed using the nametag transmitters on which the names of the users are displayed, and the pairing task between the smartphones and the nametag transmitters can be reliably executed based on this association. This makes it possible to significantly reduce the risk of a pairing error.

Here, if display of the name or the like of the user is to be affixed to the nametag transmitter, a nametag may also be printed for each user from the printer 50 connected to the management apparatus 40 via the network 200. In this case, it is desirable to perform sticker printing such that directly affixation to the nametag transmitter is possible. It is also possible to print the smartphone number to be used and the identification information in addition to the name of the user on the nametag to be adhered.

Note that if a nametag transmitter that simultaneously performs detection of biological signals at multiple sites and transmits multiple biological signals is needed for one user, setting is performed by diving the rows for each corresponding site. If one smartphone can be paired with multiple nametag transmitters, it is possible to collect and transmit biological signals at multiple sites with one smartphone per user.

The patients (users) performing rehabilitation wear the smartwear 2 until a predetermined amount of time is reached, and then gather at a predetermined location. Then, the patients attach the nametag transmitters that were given by the medical staff and on which their names are written to their smartwear 2.

When the nametag transmitters 10 are attached, the smartwear 2 and the nametag transmitters 10 are electrically connected, and the biological information such as the vital signals are acquired in the nametag transmitters 10. The acquired biological information such as the vital signals is accumulated in the memory 18 built into the nametag transmitter 10 and is transmitted to the smartphone 30 paired by the wireless communication unit 14.

Second Embodiment

Figure 7:
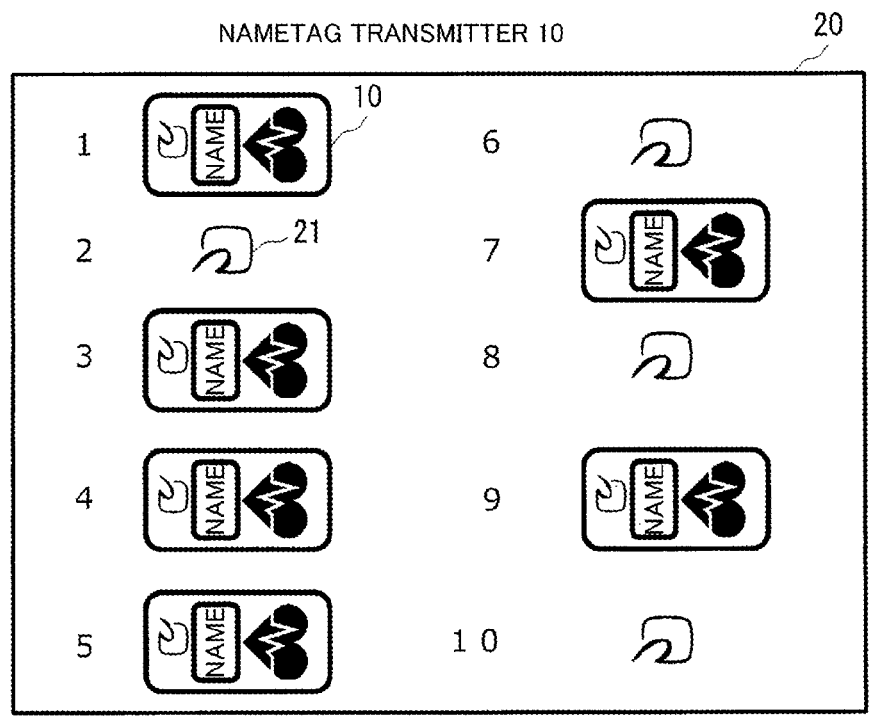
FIG. 7 is a diagram showing an exemplary configuration of a storage box according to a second embodiment of the present invention.

FIG. 7 is a diagram showing an exemplary configuration of a storage box according to a second embodiment of the present invention.

Similarly to the first embodiment, the nametag transmitters (10-1 to 10-8) are stored and managed in the storage box 20 before being attached to the smartwear. On the management screen of the management apparatus 40, identification information (IDs) of the nametag transmitters (10-1 to 10-8) stored at the storage positions is displayed in the rows corresponding to the storage position numbers (No. 1, No. 2, . . . ) in the storage box 20, similarly to the first embodiment.

As shown in FIG. 7, in the second embodiment, near-field wireless communication units 21 are built into the storage box 20 in correspondence with the positions of the stored nametag transmitters 10. The identification information (IDs) of the nametag transmitters 10 read by the near-field wireless communication units 21 is associated with the storage position numbers of the storage box 20. This correspondence information between the identification information (IDs) of the nametag transmitters 10 and the storage position numbers of the storage box 20 is transmitted from the storage box 20 to the management apparatus 40 through the network 200, and is displayed on the management screen of the management apparatus 40.

The input of the identification information such as the names of the patients (users) who are to perform rehabilitation or the like, the association of the users with the smartphones, and the pairing task between the smartphones and the nametag transmitters, which are performed in the management apparatus 40, are the same as in the first embodiment.

Third Embodiment

Figure 8:
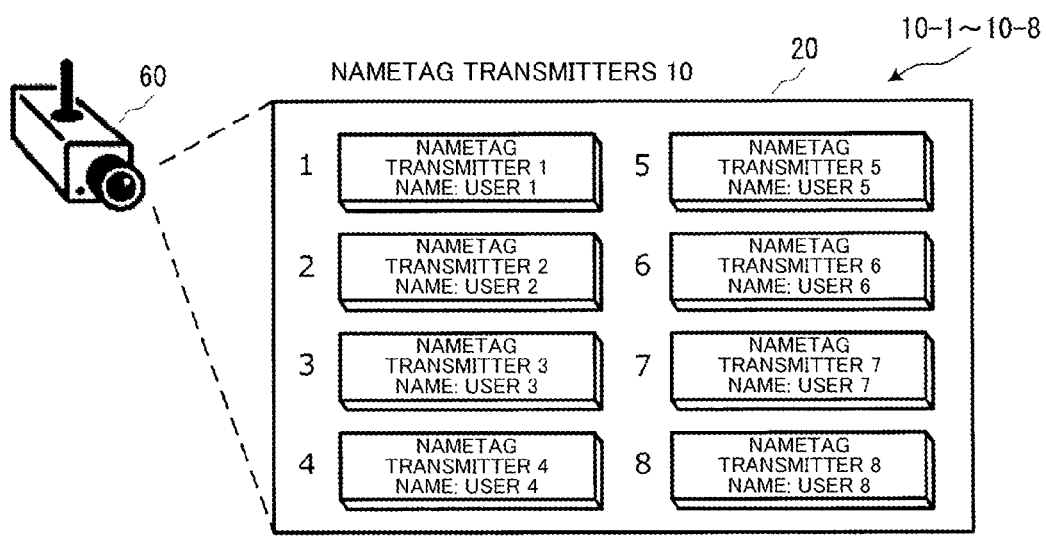
FIG. 8 is a diagram showing an exemplary configuration of a storage box according to a third embodiment of the present invention.

FIG. 8 is a diagram showing an exemplary configuration of a storage box according to a third embodiment of the present invention.

Similarly to the first and second embodiments, the nametag transmitters (10-1 to 10-8) are stored and managed in the storage box 20 before being attached to the smartwear. On the management screen of the management apparatus 40, identification information (IDs) of the nametag transmitters (10-1 to 10-8) stored at the storage positions is displayed in the rows corresponding to the storage position numbers (No. 1, No. 2, . . . ) in the storage box 20, similarly to the first embodiment.

As shown in FIG. 8, the storage box 20 of the third embodiment is understood as image information captured by a camera 60 installed at another position. The identification information of the nametag transmitters (10-1 to 10-8) and the storage position numbers of the storage box 20 are associated with each other and displayed on the management screen. The medical staff can register the correspondence information of the storage position numbers and the identification numbers of the nametag transmitters 10 on the management screen based on the image information of the storage box 20.

The input of the identification information such as the names of the patients (users) who are to perform rehabilitation or the like, the association of the users with the smartphones, and the pairing task between the smartphones and the nametag transmitters, which are performed in the management apparatus 40, are the same as in the first and second embodiments.

As described above, according to the present embodiment, the tasks to be performed by the user and the tasks to be performed by the medical staff in the pairing task are performed independently, and therefore it is possible to reduce the amount of waiting time of the user and it is possible to realize an increase in the efficiency of the pairing task. More specifically, the nametag transmitters to be paired with the smartphones to be used by the users are associated and managed using the nametag transmitters on which the names of the users are written. Since the pairing task between the smartphones and the nametag transmitters is realized based on this association, it is possible to significantly reduce the risk of a pairing error. Since the association with the users and the pairing with the smartphones can be reliably executed before being attached to the smartwear of the users based on this association, it is possible to significantly reduce the risk of a pairing error.

INDUSTRIAL APPLICABILITY

Embodiments of the present invention can be used in a system for managing smartwear for acquiring biological information of a patient, a worker, or the like at a medical facility, a work site, or the like.

REFERENCE SIGNS LIST

1 User (patient)
2 Smartwear
3, 3-1, 3-2 Electrode
10, 10-1 to 10-8 Nametag transmitter
20 Storage box
30, 30-A to 30-C Smartphone
40 Management apparatus
100 Smartwear management system.

The invention claimed is:

1. A nametag transmitter, comprising:
   a receiver configured to receive biological information from an electrode of smartwear;
   a wireless communication device configured to transmit the biological information to a data collection apparatus;
   a display configured to display identification information for specifying a user of the smartwear; and
   a connection portion configured to be attached to the smartwear, wherein the nametag transmitter is configured to be attached to the smartwear after pairing between the wireless communication device and the data collection apparatus has been carried out, wherein a near-field wireless communication device is installed at a storage position of the nametag transmitter when the nametag transmitter is stored in a storage box, and wherein a management apparatus is configured to:
acquire, from the storage box, correspondence information between storage position information of the storage position at which the nametag transmitter is stored in the storage box and identification information of the nametag transmitter; and
associate and manage the storage position information of the storage position at which the nametag transmitter is stored in the storage box and the identification information of the nametag transmitter.

2. The nametag transmitter of claim 1, wherein the nametag transmitter is configured to be stored in the storage box with a plurality of other nametag transmitters before being attached to the smartwear.

3. The nametag transmitter of claim 2, wherein the management apparatus is further configured to associate and manage the storage position information in the storage box, the identification information of the nametag transmitter, identification information of the data collection apparatus, and the identification information of the user.

4. A smartwear management system configured to manage smartwear including an electrode for detecting biological information, the smartwear management system comprising:
a nametag transmitter including:
a receiver configured to receive biological information from an electrode of smartwear;
a wireless communication device configured to transmit the biological information to a data collection apparatus;
a display configured to display identification information for specifying a user of the smartwear; and
a connection portion configured to be attached to the smartwear;
a storage box in which the nametag transmitter is configured to be stored before being attached to the smartwear; and
a management apparatus configured to associate and manage storage position information in the storage box, identification information of the nametag transmitter, identification information of the data collection apparatus paired with the wireless communication device, and the identification information of the user, wherein the data collection apparatus is paired with the wireless communication device prior to attaching, with the connection portion, the nametag transmitter to the smartwear.

5. The smartwear management system according to claim 4, wherein the management apparatus is configured to:
transmit correspondence information between the identification information of the user and the data collection apparatus to the data collection apparatus; and
transmit pairing information between the data collection apparatus and the nametag transmitter to the data collection apparatus.

6. The smartwear management system according to claim 4, wherein:
a near-field wireless communication device is installed at a storage position of the nametag transmitter in the storage box; and
from the storage box, the management apparatus acquires correspondence information between the storage position information of the storage position at which the nametag transmitter is stored and the identification information of the nametag transmitter acquired by the near-field wireless communication device.

7. A smartwear management method to be performed by a smartwear management system for managing smartwear including an electrode for detecting biological information, wherein the smartwear management system includes:
a nametag transmitter including:
a receiver configured to receive biological information from an electrode of smartwear;
a wireless communication device configured to transmit the biological information to a data collection apparatus;
a display configured to display identification information for specifying a user of the smartwear; and
a connection portion configured to be attached to the smartwear; and
a storage box in which the nametag transmitter is to be stored before being attached to the smartwear, wherein the method comprises:
associating and managing, by the smartwear management system, storage position information in the storage box, identification information of the nametag transmitter, identification information of the data collection apparatus paired with the wireless communication device, and the identification information of the user; and
attaching, with the connecting portion, the nametag transmitter to the smartwear after the data collection apparatus is paired with the wireless communication device.

8. The smartwear management method according to claim 7, further comprising transmitting, by the smartwear management system, correspondence information between the identification information of the user and the data collection apparatus to the data collection apparatus.

9. The smartwear management method according to claim 7, further comprising pairing information between the data collection apparatus and the nametag transmitter to the data collection apparatus.

10. The smartwear management method according to claim 7, wherein:
a near-field wireless communication device is installed at a storage position of the nametag transmitter in the storage box, and
the method further comprises acquiring, from the storage box by the smartwear management system, correspondence information between the storage position information of the storage position at which the nametag transmitter is stored and the identification information of the nametag transmitter acquired by the near-field wireless communication device.

* * * * *